(12) United States Patent
Chawla (10) Patent No.: US 7,249,600 B2
(45) Date of Patent: Jul. 31, 2007

(54) MEDICAMENT PACKAGING AND DISPENSER

(75) Inventor: Brindra Paul Singh Chawla, Nottingham (GB)

(73) Assignee: Technology Innovation Limited, Nottingham (GB)

(*) Notice: Subject to any disclaimer, the term of this patent is extended or adjusted under 35 U.S.C. 154(b) by 614 days.

(21) Appl. No.: 10/498,331

(22) PCT Filed: Dec. 11, 2002

(86) PCT No.: PCT/GB02/05614

§ 371 (c)(1),
(2), (4) Date: Jun. 12, 2004

(87) PCT Pub. No.: WO03/051439

PCT Pub. Date: Jun. 26, 2003

(65) Prior Publication Data

US 2005/0006273 A1    Jan. 13, 2005

(30) Foreign Application Priority Data

Dec. 14, 2001  (GB) ................... 0130055.7

(51) Int. Cl.
*A61M 15/00* (2006.01)
*A61M 16/00* (2006.01)
*A61M 15/08* (2006.01)
*B05D 7/14* (2006.01)
*B65D 83/06* (2006.01)

(52) U.S. Cl. .................. 128/203.15; 128/203.19; 128/203.23

(58) Field of Classification Search ........... 128/203.15, 128/203.19, 203.21, 203.23; 222/105, 183, 222/206, 212
See application file for complete search history.

(56) References Cited

U.S. PATENT DOCUMENTS 2,470,296 A   5/1949  Fields (Continued)

FOREIGN PATENT DOCUMENTS

DE          1039193          6/1955

(Continued)

OTHER PUBLICATIONS

PCT/GB97/03478, Jun. 25, 1998, Chawla.

(Continued)

*Primary Examiner*—Justine R. Yu
*Assistant Examiner*—Kristen C. Matter
(74) *Attorney, Agent, or Firm*—Woodling, Krost and Rust (57) ABSTRACT

A medicament package comprises a medicament container (10) and a holder (20) within which the medicament container (10) is closely received. The holder (20) comprises a support (25) of a rigid material. The support (25) has an opening, to the periphery of which an enclosure (21) is bonded. The medicament container (10) is closely received within the enclosure (21) such that the material of the enclosure (21) seals openings formed in the container (10). The container (10) can be dispensed from the package into a delivery device by pressure applied to the enclosure (21).

23 Claims, 7 Drawing Sheets

U.S. PATENT DOCUMENTS

| | | |
|---|---|---|
| 2,534,636 A | 12/1950 | Stirn |
| 2,642,063 A | 6/1953 | Brown |
| 3,155,573 A | 11/1964 | Fowler |
| 3,669,113 A | 6/1972 | Altounyan et al. |
| 3,899,121 A | 8/1975 | Herbetko |
| 4,137,914 A | 2/1979 | Wetterlin |
| 4,570,630 A | 2/1986 | Elliot et al. |
| 4,841,964 A | 6/1989 | Hurka et al. |
| 4,860,740 A | 8/1989 | Kirk |
| 5,415,162 A | 5/1995 | Casper |
| 5,522,383 A | 6/1996 | Calvert et al. |
| 5,524,613 A | 6/1996 | Haber et al. |
| 5,562,918 A | 10/1996 | Stimpson |
| 5,778,873 A | 7/1998 | Braithwaite |
| 5,797,391 A | 8/1998 | Cook et al. |
| 5,823,182 A | 10/1998 | Van Oort |
| 5,873,360 A | 2/1999 | Davies |
| 5,881,719 A * | 3/1999 | Gottenauer et al. .... 128/203.15 |
| 5,896,855 A | 4/1999 | Hobbs et al. |
| 6,089,227 A | 7/2000 | Nilsson |
| 6,092,648 A | 7/2000 | Sellars |
| 6,230,707 B1 | 5/2001 | Horlin |
| 6,328,034 B1 | 12/2001 | Eisele et al. |
| 6,418,926 B1 | 7/2002 | Chawla |
| 2002/0065256 A1 | 5/2002 | Karlsson et al. |
| 2005/0115562 A1 | 6/2005 | Chawla |
| 2006/0172009 A1 | 8/2006 | Chawla |

FOREIGN PATENT DOCUMENTS

| | | |
|---|---|---|
| EP | 0254394 | 1/1988 |
| EP | 0385156 | 9/1990 |
| EP | 0525 720 A1 | 2/1993 |
| EP | 1 016 399 A2 | 7/2000 |
| EP | 1 172 122 A1 | 1/2002 |
| EP | 1241108 | 9/2002 |
| GB | 2264237 A | 2/1992 |
| GB | 2253200 | 9/1992 |
| WO | WO91/19524 | 12/1991 |
| WO | WO 92/16249 | 10/1992 |
| WO | WO 94/19041 | 9/1994 |
| WO | WO 95/16483 | 6/1995 |
| WO | WO 98/26828 | 6/1998 |
| WO | WO 00/35522 | 6/2000 |
| WO | WO 02/085281 | 10/2002 |
| WO | WO 03/051744 | 6/2003 |
| WO | WO 03/075988 | 9/2003 |

OTHER PUBLICATIONS

PCT/GB02/01728, Apr. 12, 2002, Chawla.

* cited by examiner

MEDICAMENT PACKAGING AND DISPENSER

BACKGROUND OF THE INVENTION

This invention relates to packaging and delivery devices for medicaments, in particular to medicament packaging for use in delivery devices for the administration of medicaments by inhalation.

The most common methods of administering powdered medicament by inhalation are pressurized aerosol inhalers and dry powder inhalers. Conventional dry powder inhalers use medicament packaged in a gelatine capsule. An improved method of administration, however, is disclosed in WO 98/26828.

WO 98/26828 discloses several delivery devices for use with medicament containers that contain pre-formed openings through which medicament is dispensed within the delivery device. The delivery devices all comprise a mouthpiece, air inlet means and a chamber in which the medicament container is located. In use, air is drawn into the chamber, causing the medicament container to follow an orbital path around the chamber. In this way the medicament is dispensed through the openings of the medicament container and medicament entrained with air is drawn out of the chamber and through the mouthpiece. The disclosed delivery devices include single-use delivery devices pre-loaded with a medicament container and multi-use delivery devices in which a medicament container is inserted into the chamber before use.

In addition, various medicament packages comprising a medicament container and holder are disclosed, in which the openings in the medicament container are sealed by the holder. The medicament containers disclosed generally comprise an inverted cup, having at least one opening, and a closure. The holders disclosed include: an O-ring of elastomeric material which fits closely around the medicament container; a plastics sheet containing circular apertures whose periphery is formed by a ring of elastomeric material into which the medicament containers are pressed with a close, interference fit; and a sheet of resilient plastics or elastomeric material having circular recesses into which the medicament containers are pressed.

The medicament packages and delivery devices disclosed in WO 98/26828 represent a considerable advance over the prior art, but are nonetheless susceptible to further improvement. In particular, single-use delivery devices may be considered wasteful as they can only be used once, the whole device then being discarded. Also, the medicament packages may not retain the medicament containers as securely as might be desired.

SUMMARY OF THE INVENTION

There has now been devised an improved form of medicament package and medicament delivery device that overcome or substantially mitigate the above-mentioned and/or other disadvantages of the prior art.

According to a first aspect of the invention, there is provided a holder for a container containing a unit dose of a powdered medicament, the holder comprising a support of a rigid material, the support having an opening formed therein, and an enclosure of a deformable material, the enclosure being bonded to the periphery of the opening and extending therefrom such that the opening constitutes an open mouth of the enclosure.

In a related aspect of the invention, there is provided a medicament package, the package comprising a holder as defined in the immediately preceding paragraph and a medicament container containing a unit dose of a medicament in powder form and having at least one dispensing aperture, the container being closely received within the enclosure such that the at least one dispensing aperture is sealed by the material of the enclosure.

The medicament package according to the invention is advantageous primarily in that the deformable nature of the enclosure means that the medicament container may be released from the enclosure with ease, using finger pressure. Until the container is so released, the material of the enclosure effectively seals the dispensing aperture(s) in the container, preventing premature egress of medicament and ingress of moisture. It is thus unnecessary to provide further sealing means, eg sealing foils or the like, that seal the opening in the support so as completely to enclose the medicament container. This facilitates both the manufacturing process (in that it is not necessary to apply such a further seal), and use of the medicament package (in that it is not necessary to rupture or remove such a further seal). In addition, the holder may be fashioned such that it is received by a delivery device, thereby facilitating loading the device and administration of medicament. In addition, the medicament package is easier to handle and store due to the rigid support.

Preferably, the enclosure contacts the medicament container around the entire periphery of the medicament container, and not just in the regions of the dispensing aperture(s). Effective sealing of the dispensing aperture(s) by insertion of the medicament container into the enclosure then does not depend on the orientation of the medicament container within the enclosure.

The rigid support is preferably made of plastics material. Any suitably rigid plastics material may be used. Preferred materials include polyolefins, the currently most preferred material being polypropylene. The deformable enclosure is preferably of elastomeric material. The elastomeric material is preferably water resistant and non-toxic. A particularly suitable elastomeric material is a medical grade thermoplastic rubber, eg that referred to as SANTOPRENE (Advanced Elastomer Systems NV/SA, Leicester, United Kingdom).

The rigid support and enclosure may be injection moulded in a two-step process. In such a process, the rigid support is preferably injection moulded in a first step. The enclosure is then injection moulded onto the pre-formed support. The materials used for the support and the enclosure are preferably chosen such that they adhere when the second material is moulded onto the first. The preferred materials polypropylene and thermoplastic rubber adhere in that fashion. In other embodiments, the enclosure may be bonded to the support by other techniques, eg using adhesive, plastics welding techniques, etc.

The package may contain a single medicament container, ie the holder may comprise a single enclosure. In such a case, the holder is preferably formed for engagement with a delivery device such that the holder is held stationary within the device and the container may be released from the enclosure directly into the interior of the device.

The enclosure preferably has the form of a cup. In general, the shape of the cup will conform to that of the medicament container. Most preferably the enclosure fits closely around at least that part of the container which is formed with the dispensing aperture(s). The open mouth of the enclosure may extend beyond the rigid support.

The medicament container preferably comprises a cup and a closure which fit together with a close, interference fit. The medicament container is preferably made of plastics material of low moisture permeability and is most preferably made of high density polyethylene. The cup and the closure of the medicament container are preferably injection moulded.

The medicament container is most commonly generally cylindrical, most preferably taking the form of a drum. The drum may be relatively squat, having a depth that is comparable to, or less than, its diameter. The depth of the container is preferably not greater than 1.5 times, and is more preferably less than, its diameter. The upper and lower faces of the container may be flat or, particularly in the case of the upper face, may be convex or domed.

The medicament container may have a single compartment that holds a unit dose of medicament. Alternatively, the medicament container may comprise two or more compartments, each of which contains a dose of the same or different medicaments. Medicament containers of this type are described in WO 02/085281, the teaching of which is incorporated herein by reference. In one particular embodiment, the medicament container takes the form of a generally cylindrical drum divided transversely into two cylindrical compartments, each containing a unit dose of medicament, the two medicaments being administered together when the container is introduced into a delivery device.

Individual medicament packages, each containing a single medicament container as described above, may be stored in a storage device. Such a storage device preferably comprises a sheet of plastics material including a recess for each medicament package. The recess is dimensioned such that a medicament package may be closely received within the recess with an interference fit. Most preferably, the medicament packages are inserted into, or removed from, the storage device by a sliding action. The storage device is preferably injection moulded.

In other embodiments, the medicament package may contain a plurality of medicament containers. In such a case, the rigid support may comprise a sheet of plastics material having a corresponding number of openings, each opening having an enclosure bonded to its inner edge. The medicament package of this form may again be formed by a two-step injection moulding process, as described above.

As well as serving as packages for the medicament, preventing egress of medicament and ingress of water, individual medicament packages according to the invention, ie medicament packages containing a single medicament container, may also serve as components of delivery devices. In particular, such a package may be engaged with a delivery device such that the package constitutes a closure for a chamber within the device. The device may thereby be preloaded with a medicament container, the container then being released from the package directly into the chamber immediately before use. After use, the package (including the spent container) can be removed from the device and discarded. The device may then be reloaded with a fresh package, for later use.

According to another aspect of the invention, there is thus provided a delivery device for the delivery of powdered medicament by inhalation, the delivery device comprising a chamber adapted to receive a medicament container containing a unit dose of medicament in powder form, air inlet means by which air can be drawn into the chamber, a mouthpiece by which air can be drawn out of the chamber, and a medicament package as described above, the package being engageable with the chamber so as to close the chamber and such that the medicament container can be released from the package into the chamber.

To facilitate engagement of the package with the rest of the device, the device is preferably provided with formations by which the package is retained, eg with a snap or interference fit.

In preferred embodiments, the package is slid into position, along grooves formed in the device. In such a case, the device is preferably formed with guide means to facilitate location and engagement of the package. Such guide means may take the form of a depression that is formed such that a medicament package may be slid along it until the medicament package is closely engaged.

In devices in which the medicament package forms part of the device, the enclosure may have one or more openings through which air may be drawn into the chamber after the container has been released from the package. Such airflow may augment and optimise the flow of air through the chamber during use of the device. Typically, an opening may be formed at the apex of the enclosure.

The invention will now be described in greater detail, by way of illustration only, with reference to the accompanying drawings, in which.

DETAILED DESCRIPTION OF THE INVENTION

DETAILED DESCRIPTION OF THE INVENTION

A first embodiment of a medicament package according to the invention comprises a medicament container (10) and a holder (20) within which the medicament container (10) is closely received.

Figure 1:
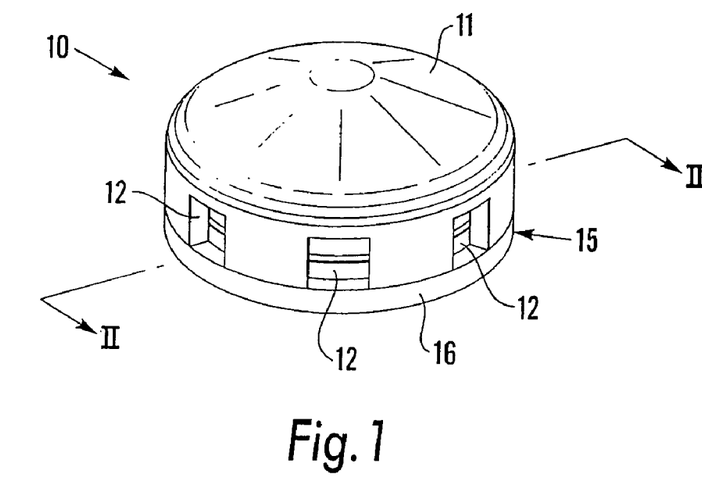
FIG. 1 is a perspective view of a medicament container forming part of a first embodiment of a medicament package according to the invention.
Figure 2:
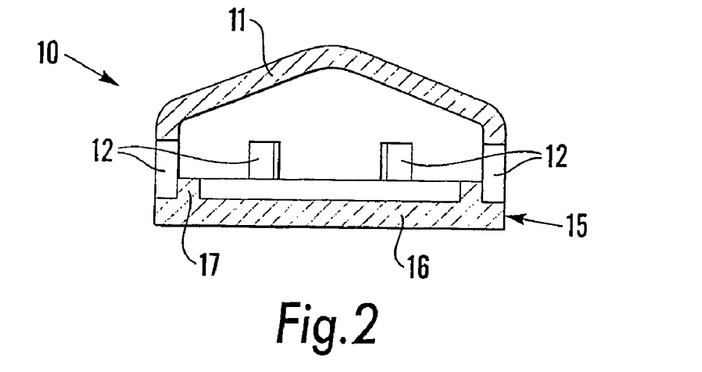
FIG. 2 is a sectional view on the line II-II in FIG. 1.
Figure 3:
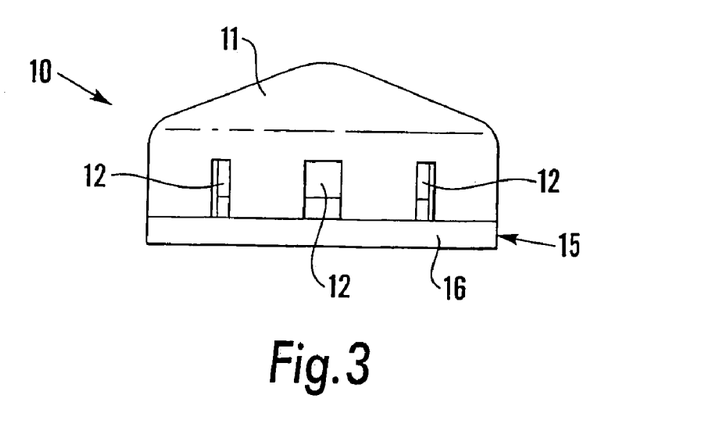
FIG. 3 is a side view of the medicament container.

Referring first to FIGS. 1 to 3, the medicament container (10) comprises an inverted cup (11) and a closure (15), both of plastics material. The cup (11) comprises a cylindrical main body with a diameter greater than its height, an open lower end and a closed upper end (as viewed in FIG. 1) that is of generally domed or conical shape. The apex of the cup (11) is of rounded shape.

The cylindrical main body of the cup (11) contains a series of equiangularly spaced rectangular openings (12) which extend upwardly from the open end of the cup (11) along the majority of the height of the main body, as shown most clearly in FIGS. 1 and 3.

The closure (15) comprises a circular plate (16) with a diameter identical to the external diameter of the cup (11) and an upstanding rim (17) that is received closely within the lower end of the cup (11) with an interference fit. The rim (17) extends upwardly to occlude the lower part, but only the lower part, of each opening (12) in the cup (11), as shown in FIG. 2.

Figure 4:
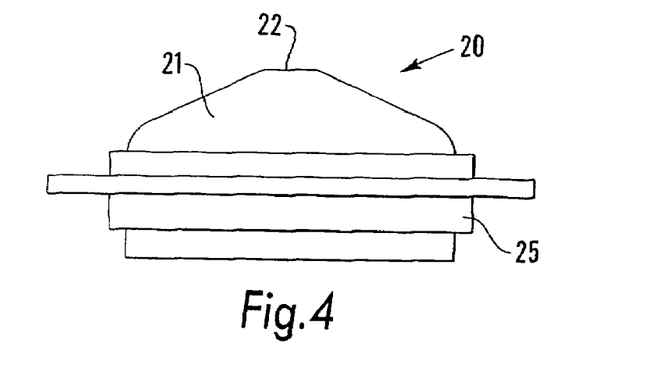
FIG. 4 is a side view of a holder that, together with the medicament container, forms the medicament package.
Figure 5:
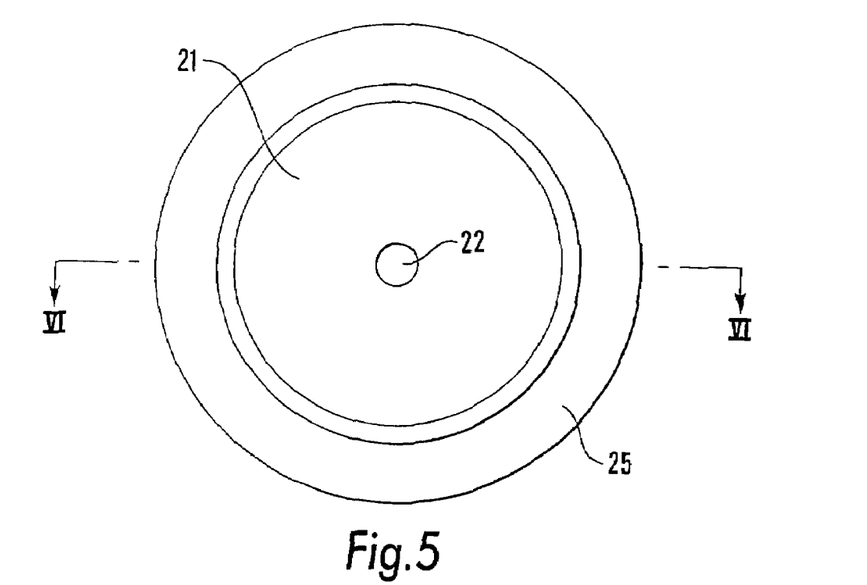
FIG. 5 is a plan view of the holder.
Figure 6:
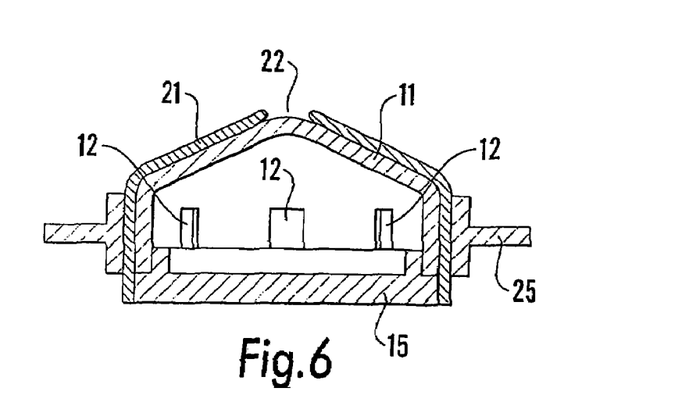
FIG. 6 is a sectional view of the holder engaged with the medicament container, on the line VI-VI in FIG. 5.

Turning now to FIGS. 4 to 6, the holder (20) comprises an enclosure (21) of elastomeric material and a support ring (25) of rigid plastics material. The support ring (25) comprises an annular plate and a vertically (as viewed in FIG. 4) orientated upper and lower skirt on the inner edge of the annular plate. The support ring (25) fits closely around the outside of the cylindrical main body of the enclosure (21). The lower part of the enclosure (21) projects a short distance beyond the lower edge of the support ring (25).

The enclosure (21) comprises a cylindrical main body, an open lower end and an upper end (as viewed in FIG. 4) that is of generally conical shape. The enclosure (21) is of similar shape to the cup (11) of the medicament container (10), and is dimensioned such that the medicament container (10) is closely received within the enclosure. The uppermost point of the enclosure (21) contains a circular aperture (22). The enclosure (21) fits closely around the majority of the outside of the medicament container (10) except the apex of the cup (11) and the underside of the closure (15), as shown most clearly in FIG. 6.

Referring to FIG. 6, the assembled medicament package comprises the medicament container (10) fitting closely within the holder (20) such that the openings (12) in the medicament container (10) are sealed by the elastomeric material of the enclosure (21). It is not necessary to apply a further or secondary seal, eg in the form of a foil that extends across the mouth of the enclosure (21) and completely encloses the medicament container (10). Due to the deformable nature of the enclosure (21), the medicament container (10) may be dispensed from the holder (20) into an inhaler device by exerting downward pressure on the uppermost point of the enclosure (21) whilst the support ring (25) is held stationary (as described in more detail below).

The medicament container (10) is approximately 10 mm in diameter and 7 mm in depth. The holder (20) is approximately 16 mm in diameter and 7 mm in depth.

The holder (20) is manufactured using a two-step injection moulding process. The support ring (25) is moulded first, in a suitably rigid plastics material such as polypropylene. The enclosure (21) is then formed by injection of an elastomeric material that bonds to the pre-formed support ring (25). A suitable elastomeric material is the medical grade thermoplastic rubber of the type known as SANTOPRENE, from Advanced Elastomer Systems.

Figure 7:
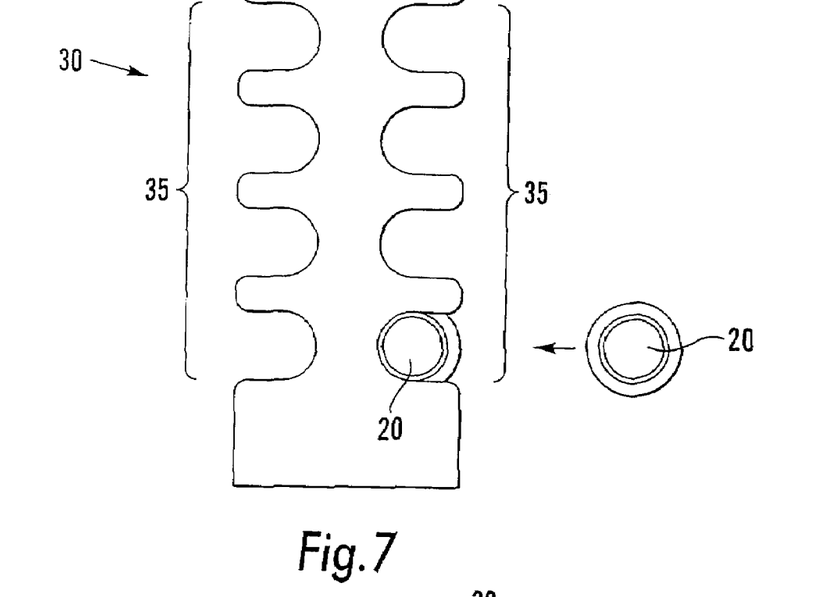
FIG. 7 is a plan view of a medicament package storage device engaged with a single medicament package of the form illustrated in FIGS. 4 to 6.
Figure 8:
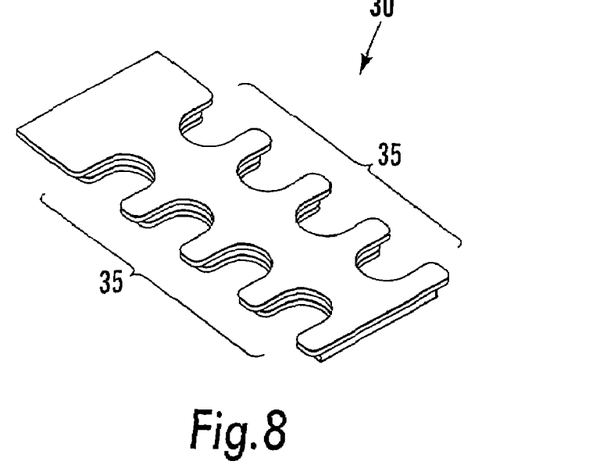
FIG. 8 is a perspective view of the medicament package storage device.
Figure 9:
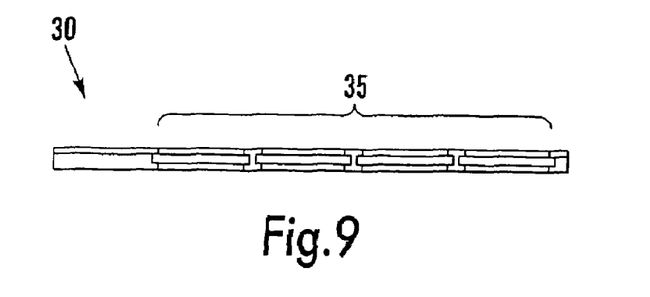
FIG. 9 is a side view of the medicament package storage device.

Turning now to FIGS. 7, 8 and 9, a medicament package storage device (30) according to the invention is formed as a single body of moulded plastics material and is generally planar and rectangular overall shape having approximate dimensions of 90 mm length, 35 mm width and 2 mm thickness.

The storage device (30) is designed to hold eight medicament packages of the type described above. Each major edge of the storage device (30) is formed with a series of four generally C-shaped cut-outs or recesses (35). The dimensions of the recesses (35), in particular the width of the recess and the radius of its innermost part, are such that the support ring (25) of a medicament package can be slotted into the recess (35) and be retained with an interference fit. The upper and lower parts of the recesses (35) correspond in size to the external diameter of the skirt of the support ring (25), the central part of the recess being somewhat enlarged so as to receive the annular plate. In addition, the lower part of the storage device (30) is of reduced width, being approximately 6 mm narrower than the upper part.

Medicament packages (20) can be introduced into the storage device (30) by sliding them laterally into the C-shaped cut-outs. Normally, the medicament packages will be disposed in the storage device (30) with the open ends of the respective enclosures directed towards the underside (as viewed in the FIGS.) of the storage device (30). A medicament package can be removed from the storage device (30) simply by application of finger pressure to the part of the medicament package that projects above the upper surface of the storage device (30).

Figure 10:
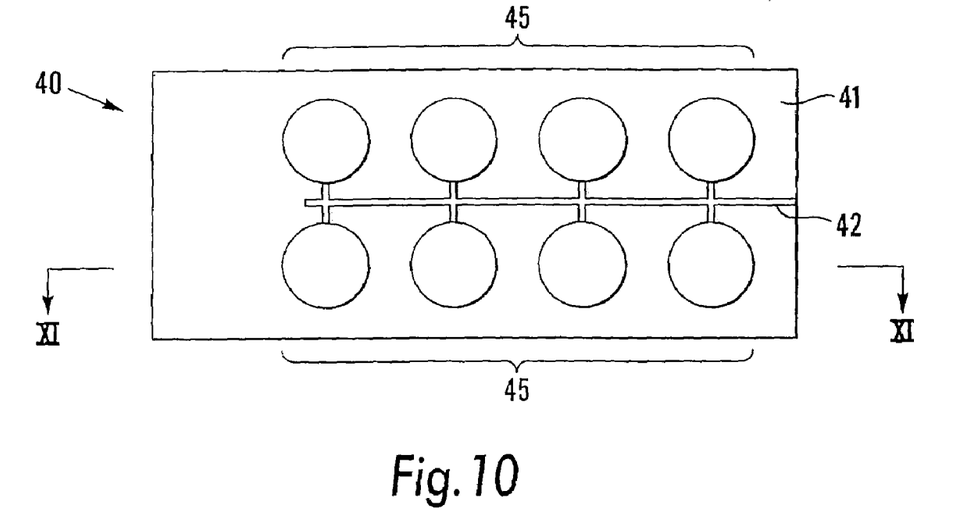
FIG. 10 is a plan view of a holder that forms part of a second embodiment of a medicament package according to the invention.
Figure 11:
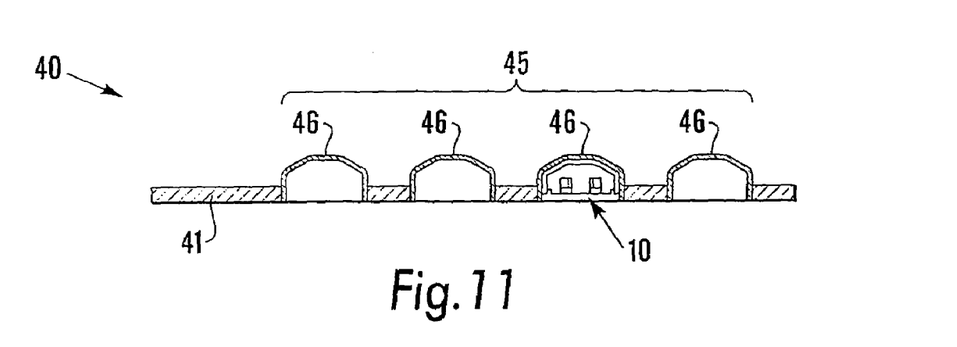
FIG. 11 is a sectional view, on the line XI-XI in FIG. 10, of the holder of FIG. 10 engaged with a single medicament container.
Figure 12:
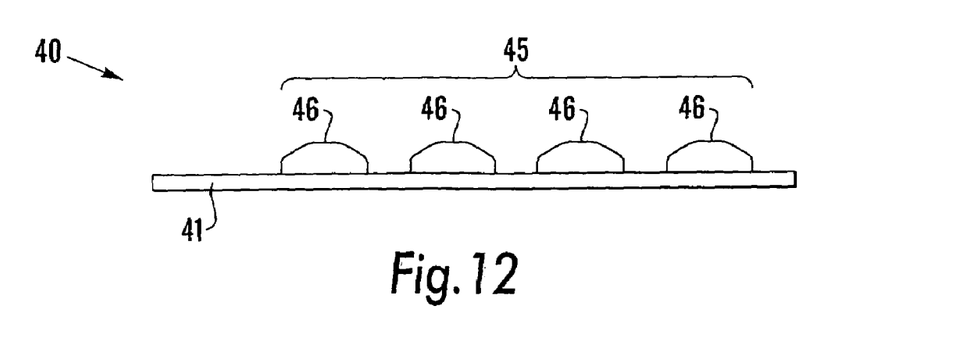
FIG. 12 is a side view of the holder of FIG. 10.

Turning now to FIGS. 10, 11 and 12, a holder that forms part of a second embodiment of a medicament package according to the invention is generally designated 40. The holder (40) comprises a rectangular sheet of plastics material (41) containing a series of circular apertures (45) positioned longitudinally along each half of the rectangular sheet (41). The rectangular sheet (41) is approximately 85 mm in length, 40 mm in width and 2 mm in thickness.

Like the first embodiment, the holder (40) is formed in a two-step injection moulding process. The sheet (41) is moulded first in a rigid material. Elastomeric material is the injected along a groove (42) along the longitudinal axis of the upper surface of the rectangular sheet (41) which branches into each aperture (45), as shown most clearly in FIG. 10. The elastomeric material forms an enclosure (46) bonded to the internal edge of each aperture (45). The enclosure (46) is of similar shape to the enclosure (21) of the medicament holder (20), and is dimensioned such that a medicament container (10) is closely received, with an interference fit, within the enclosure (46). Again, the material of the enclosure (46) seals the openings in the medicament container (10), no further seal (eg a foil applied across the underside of the sheet (41)) being necessary.

Due to the deformable nature of the enclosure (46), the medicament container (10) may be dispensed from the container storage device (40) by exerting downward pressure on the uppermost point of the enclosure (46) while the rectangular sheet (41) is held stationary. A suitable inhaler (not shown), similar to that described below, may receive the rigid support such that the medicament container (10) may be dispensed directly into the chamber of said inhaler.

Turning now to FIGS. 13 to 17, a medicament inhaler according to the invention is generally designated 100. The inhaler (100) is for use with the medicament packages of the kind illustrated in FIG. 6, and comprises a main body (110) and a lid (120), both of which are moulded in plastics material and connected together by a hinge (113). The inhaler (100) is approximately 65 mm in length, 45 mm in width and 20 mm in depth.

Figure 15:
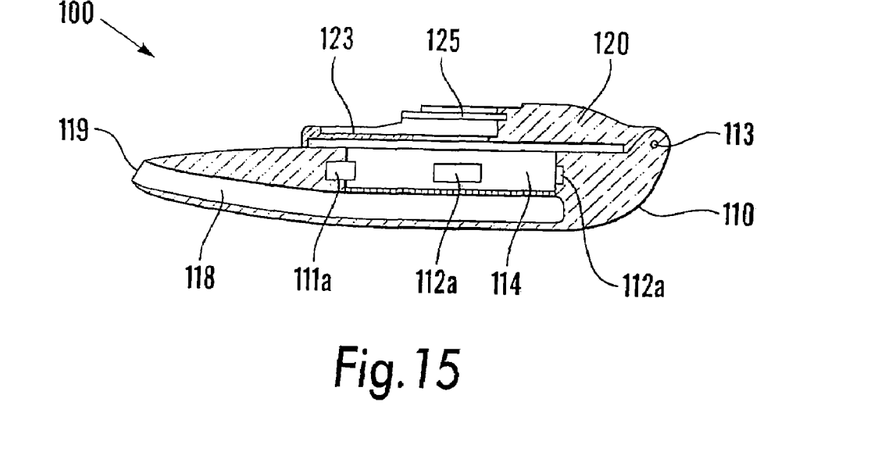
FIG. 15 is a sectional view on the line XV-XV in FIG. 13.
Figure 16:
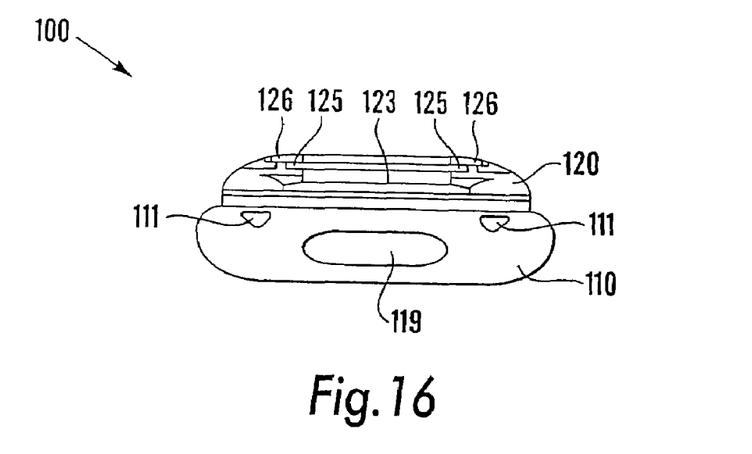
FIG. 16 is an end view of the medicament inhaler.
Figure 17:
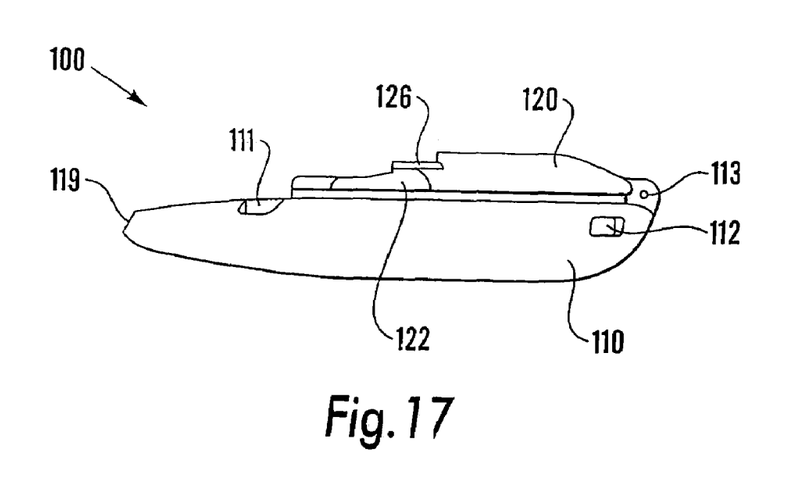
FIG. 17 is a side view of the medicament inhaler.

The main body (110) comprises a mouthpiece (119), a passageway (118), a chamber (114), conduits (111a, 112a) and air inlets (111, 112). The mouthpiece (119) is a generally elliptical opening in one end of the main body (110). The passageway (118) extends from the mouthpiece (119), through the lower part of the main body (110), towards the other end of the main body (110), as shown in FIG. 15.

The chamber (114) is cylindrical in shape with an open upper end and is positioned above the passageway (118). The chamber (114) communicates with the passageway (118) by means of a series of openings which make up a generally circular grid (115) in the centre of the base of the chamber (114), as shown in FIG. 14.

Figure 14:
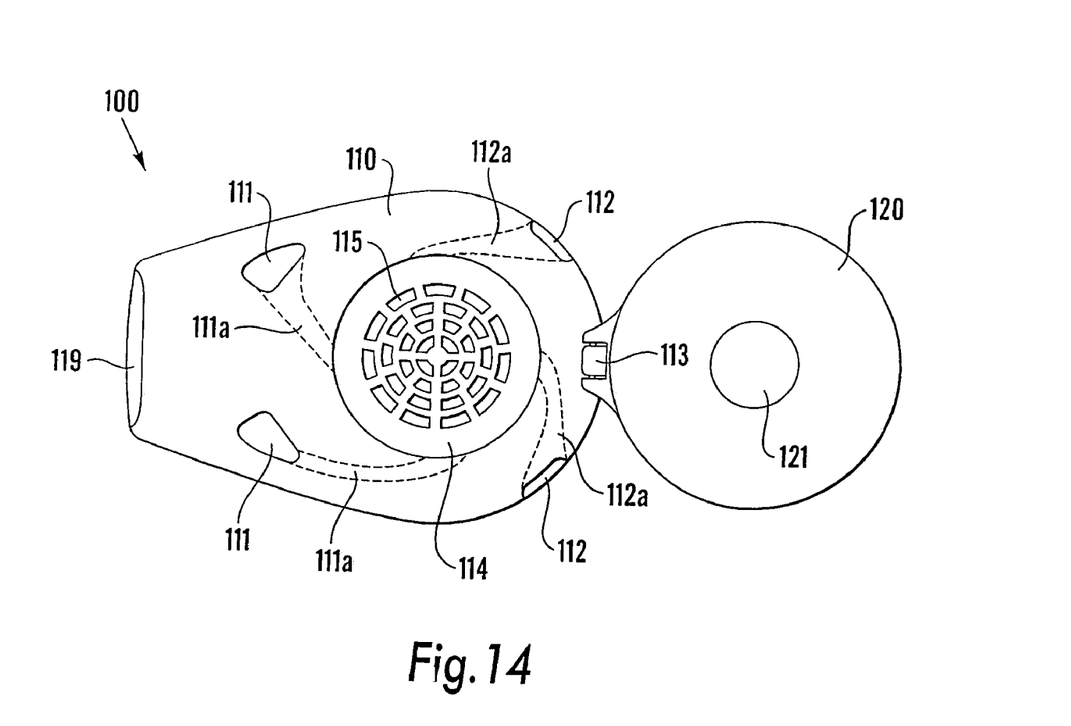
FIG. 14 is a plan view, showing hidden detail, of the medicament inhaler with the lid open.

There are two front air inlets (111) and two rear air inlets (112) which connect the wall of the chamber (114) and the exterior of the inhaler (100) by means of respective conduits (111a, 112a) which are shown by dotted lines in FIG. 14. The conduits (111a, 112a) are aligned substantially tangentially to the wall of the chamber (114) and connect to the chamber (114) at equiangularly spaced locations.

Figure 13:
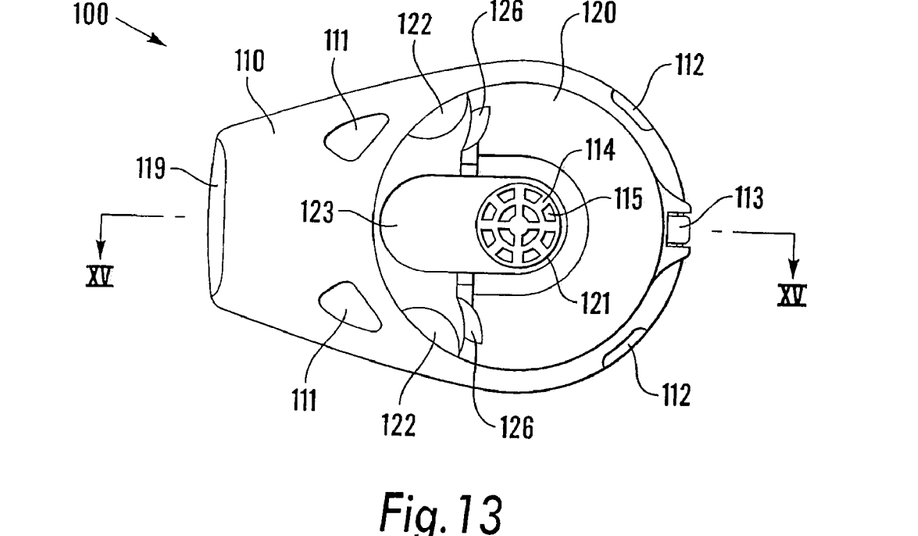
FIG. 13 is a plan view of a medicament inhaler according to the invention.

The lid (120) is of circular shape and contains a circular aperture (121) which is positioned over the centre of the chamber (114) in the main body (110) when the lid (120) is closed, The aperture (121) has a diameter such that a medicament container (10) will fit through the aperture (121) but a holder (20) will not.

The interior wall of the aperture (121) is provided with a groove (125) that is dimensioned to closely receive the annular plate of the support ring (25) of the holder (20) with an interference fit. The upper surface of the lid (120) is provided with a depression (123) which extends from the aperture (121) to the edge of the lid (120). The depression (123) is formed such that a medicament package may be slid, from a medicament package storage device (30) or otherwise, along the depression (123) into the aperture (121) until the support ring (25) of the holder (20) is closely received within the groove (125) in the aperture (121).

The lid (120) includes two grips (122) which facilitate the opening of the lid (120). When not in use, a plug (not shown) is provided which is received closely within the aperture (121) with an interference fit.

The inhaler (100) is used to deliver medicament from the medicament container (10) described earlier. In use, the lid (120) is closed and a medicament package, comprising a medicament container (10) and holder (20), is slid along the depression (123) into the groove (125) in the aperture (121) in the lid (120). The inhaler (100) is now in a loaded state.

The upper surface of the lid (120) is further provided with recesses (126) that are formed such that a medicament package storage device (30), shown in FIG. 7, may be held on the upper surface of the lid (120) in a position such that a medicament package engaged with the storage device (30) may be slid along the depression (123) into the groove (125) in the lid (120), thereby disengaging the medicament package from the storage device (30) and loading the inhaler (100).

When the patient is ready to use the inhaler (100), the patient applies manual pressure downwards on the enclosure (21) of the medicament package. This will dispense the medicament container (10) from the holder (20) into the chamber (114) of the inhaler. The patient then places the mouthpiece (119) to his or her mouth and inhales. Air is drawn through the air inlets (111, 112), along the conduits (111a, 112a) and substantially tangentially into the chamber (114). The airstream passes through the grid (115) and along the passageway (118) to the patient's mouth.

The stream of air entering the chamber (114) tangentially causes the medicament container (10) to orbit about the centre of the chamber (114). The movement of the medicament container (10) is constrained by the side wall of the chamber (114) and medicament is dispensed from within the medicament container (10) through the openings (12) in the medicament container (10) under the influence of centrifugal forces. The medicament is entrained in the airstream which passes out of the chamber (114) through the grid (115) and is inhaled by the patient.

After use, the medicament container (10) is removed from the inhaler (100) by opening the lid (120) and removing the container (10) or by shaking the inhaler (100) upside down until the medicament container (10) falls through the aperture (121). The inhaler (100) is then either reloaded with another medicament package or sealed using the plug.

Figure 18:
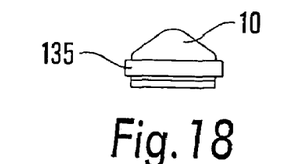
FIG. 18 is a side view of a sealing ring engaged with a medicament container.
Figure 19:
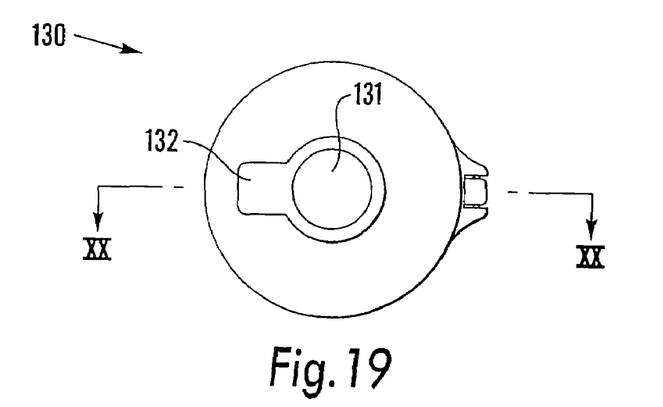
FIG. 19 is a plan view of an alternative inhaler lid.
Figure 20:
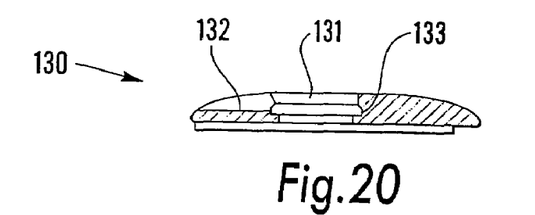
FIG. 20 is a sectional view on the line XX-XX in FIG. 19.
Figure 21:
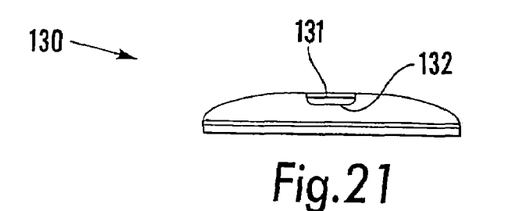
FIG. 21 is an end view of the alternative inhaler lid.
Figure 22:
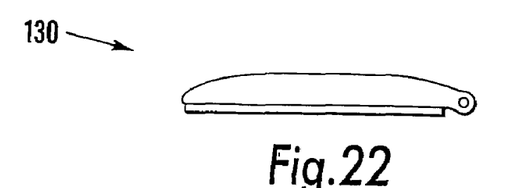
FIG. 22 is a side view of the alternative inhaler lid.

An alternative medicament package comprises a sealing ring (135) of elastomeric material which fits closely around a medicament container (10) such that the openings (12) are sealed, as shown in FIG. 18.

An inhaler for use with this medicament package has a lid (130) as shown in FIGS. 19 to 22. Again, the lid (130) is of circular shape and contains a circular aperture (131). The aperture (131) has a diameter such that a medicament container (10) will fit through the aperture (131) but the sealing ring (135) will not. The aperture (131) contains a groove (133) and an upper section with an enlarged diameter, such that the sealing ring (135) may be snap fitted from above into the groove (133) within the aperture (131).

Once the medicament package is held within the aperture (131), manual pressure downwards on the medicament container (10) will introduce the medicament container (10) to the inhaler. The sealing ring (135) is then removed from within the aperture (131) and the aperture (131) is sealed with a plug (not shown). Thereafter, the manner of use is identical to that described earlier. The lid (130) includes a depression (132) to aid the removal of the plug.

The invention claimed is:

1. A holder for a container containing a unit dose of a powdered medicament, the holder comprising a rigid support having an opening formed therein, and a deformable enclosure bonded to the periphery of the opening and extending therefrom such that the enclosure has the form of a cup and the opening constitutes an open mouth of the enclosure, the arrangement being such that a container is inserted through the open mouth of the enclosure and received by the enclosure with a close fit, and pressure applied, in use, by a user to the exterior of the enclosure deforms the enclosure and causes the container to be dispensed from the enclosure through the open mouth thereof.

2. A holder as claimed in claim 1, wherein the rigid support and the enclosure are injection moulded in a two-step process, the rigid support being injection moulded in a first step and the enclosure then being then injection moulded onto the support.

3. A holder as claimed in claim 1, wherein the support is made of polypropylene and the enclosure is made of thermoplastic rubber.

4. A holder as claimed in claim 1, which comprises a single enclosure.

5. A holder as claimed in claim 1, which comprises a plurality of enclosures.

6. A medicament package, the package comprising a holder as claimed in claim 1 and a medicament container containing a unit dose of a medicament in powder form and having at least one dispensing aperture, the container being closely received with the enclosure such that the at least one dispensing aperture is sealed by the material of the enclosure.

7. A medicament package as claimed in claim 6, wherein the medicament container comprises a cup and a closure which fit together with a close, interference fit.

8. A medicament package as claimed in claim 6, wherein the container is made of high density polyethylene.

9. A medicament package as claimed in claim 6, wherein the medicament container has the form of a drum.

10. A medicament package as claimed in claim 9, wherein the drum has a depth that is not greater than 1.5 times its diameter.

11. A medicament package as claimed in claim 6, wherein the medicament container has a single compartment that holds a unit dose of medicament.

12. A medicament package as claimed in claim 6, wherein the medicament container comprises two or more compartments, each of which contains a dose of the same or different medicaments.

13. A medicament package as claimed in claim 6, wherein the package contains a single medicament container.

14. A medicament package as claimed in claim 13, wherein the holder is formed for engagement with a delivery device such that the holder is held stationary within the device and the container may be released from the enclosure directly into the interior of the device.

15. A medicament package as claimed in claim 14, wherein the enclosure is formed with one or more openings.

16. A medicament package as claimed in claim 15, which is formed with one opening at the apex of the enclosure.

17. A plurality of medicament packages as claimed in claim 13, stored in a storage device adapted releasably to hold said medicament packages.

18. A plurality of medicament packages as claimed in claim 17, wherein the storage device comprises a sheet of plastics material including a recess for each medicament package.

19. A delivery device for the delivery of powdered medicament by inhalation, the delivery device comprising a chamber adapted to receive a medicament container containing a unit dose of medicament in powder form, air inlet means by which air can be drawn into the chamber, a mouthpiece by which air can be drawn out of the chamber, and a medicament package as claimed in claim 13, the package being engageable with the chamber so as to close the chamber and such that the medicament container can be released from the packaged into the chamber.

20. A delivery device as claimed in claim 19, wherein the device is provided with formations by which the package is retained with a snap or interference fit.

21. A delivery device as claimed in claim 19, which is formed with guide means to facilitate location and engagement of the package.

22. A medicament package as claimed in claim 6, wherein the medicament package contains a plurality of medicament containers.

23. A medicament package as claimed in claim 22, wherein the rigid support comprises a sheet of plastics material having a plurality of openings, each opening having an enclosure bonded to its inner edge.

* * * * *